United States Patent [19]

Jacobs

[11] 3,960,877

[45] June 1, 1976

[54] N-MONOSUBSTITUTED-2,3-PYRIDINEDICARBOXAMIDES, AND RELATED COMPOUNDS

[75] Inventor: Richard L. Jacobs, Perrysburg, Ohio

[73] Assignee: The Sherwin-Williams Company, Cleveland, Ohio

[22] Filed: Dec. 23, 1974

[21] Appl. No.: 536,947

Related U.S. Application Data

[63] Continuation of Ser. No. 381,770, July 23, 1973, abandoned, which is a continuation of Ser. No. 82,804, Oct. 21, 1970, abandoned, which is a continuation of Ser. No. 740,046, June 26, 1968, abandoned.

[52] U.S. Cl.................. 260/295.5 A; 260/248 AS; 260/250 A; 260/250 BN; 260/256.4 R
[51] Int. Cl.².................................... C07D 213/56
[58] Field of Search ............... 260/248 AS, 250 BN, 260/250 A, 256.4 R, 295.5 A, 244 A

[56] References Cited
UNITED STATES PATENTS

| | | | |
|---|---|---|---|
| 3,525,747 | 8/1970 | Jacobs | 260/256.4 R |
| 3,635,973 | 1/1972 | Jacobs | 260/295.5 A |
| 3,752,816 | 8/1973 | Cooke et al. | 260/256.4 F |

OTHER PUBLICATIONS

Dimitrijevic et al., Chem. Abstracts, vol. 56, (5) 4720e–f, Mar. 5, 1962.

*Primary Examiner*—Alan L. Rotman
*Attorney, Agent, or Firm*—John C. Purdue

[57] ABSTRACT

A method for producng N-monosubstituted-2,3- and 3,4-pyridinedicarboxamides and 2,3-pyrazinedicarboxamides, which is accomplished by reacting corresponding imide precursors with ammonia or primary or secondary amines in the presence of a suitable solvent such as anhydrous alcohols, ethers, dimethylformamide and the like.

3 Claims, No Drawings

N-MONOSUBSTITUTED-2,3-PYRIDINEDICARBOXAMIDES, AND RELATED COMPOUNDS

CROSS REFERENCE TO RELATED APPLICATIONS

This is a continuation of Ser. No. 381,770, filed July 23, 1973, now abandoned, which in turn was a continuation of Ser. No. 82,804, filed Oct. 21, 1970, now abandoned, which in turn was a continuation of Ser. No. 740,046, filed June 26, 1968, now abandoned.

BACKGROUND OF THE INVENTION

This invention relates to a method of preparing compounds that are useful intermediates in the production of compounds which have utility as plant growth regulators, weed killers, defoliating agents and agricultural chemicals.

In modern day agriculture, chemicals are used extensively for weed and plant control, and as defoliating agents. Many different types of chemical agents are being used, having varying degrees of herbicidal activity. While the chemicals currently used are in general adequate, they are sufficiently expensive that expense is a significant factor in their use. Therefore, new compounds and inexpensive methods for producing such compounds are constantly being sought.

In addition, while many compounds presently on the market are effective against certain species of weeds, they are ineffective against others. Thus new herbicides which have broad spectrum effectiveness against a wide variety of weeds are continually being sought.

It has been discovered that certain substituted-pyrido[3,2-d]pyrimidine-2,4(1H,3H)-diones, some analogous [2,3-d], [3,4-d] and [4,3-d] dione compounds, and certain lumazines have unexpectedly high levels of herbicidal activity.

The instant invention is directed to a method of making intermediate compounds which are used in the production of the aforementioned pyridopyrimidine diones and lumazines.

It is an object of this invention to provide a method for making intermediate compounds which are useful in the production of compounds which are effective plant growth regulators and weed killers.

It is a further object of this invention to provide a method of making compounds which are themselves weed killers.

It is a further object of this invention to provide a method of making N-monosubstituted-2,3- and 3,4- pyridinedicarboxamides, and 2,3-pyrazinedicarboxamides, and the compounds made by such method.

Other objects and benefits of this invention will be apparent from the following disclosure.

SUMMARY OF THE INVENTION

The compounds of this invention are prepared by reacting compounds having the structural formula

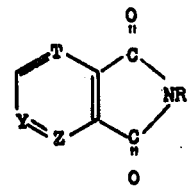

wherein each of T, Y and Z is nitrogen or CH and at least one is CH and at least one is nitrogen, and wherein when Y is nitrogen, T and Z are CH; and wherein R is hydrogen or a member of the group consisting of alkyl groups having from 1 to 8 carbon atoms, benzyl, chlorobenzyl, dichlorobenzyl, methoxybenzyl, methylbenzyl, cycloalkyl groups having from 3 to 8 carbon atoms, allyl and propargyl, with a nitrogen based compound having the formula

wherein R' and R'' are members of the group consisting of hydrogen, alkyl groups having from 1 to 8 carbon atoms, benzyl, chlorobenzyl, dichlorobenzyl, methoxybenzyl, methylbenzyl, cycloalkyl groups having from 3 to 8 carbon atoms, allyl and propargyl, wherein either R or each of R' and R'' is a hydrogen at all times; and wherein when R is not hydrogen, R' and R'' are hydrogen, said reaction being carried out in the presence of an anhydrous solvent at a temperature within the range of from 0°C. to 50°C.

The method of the invention and the compounds produced can be illustrated as follows:

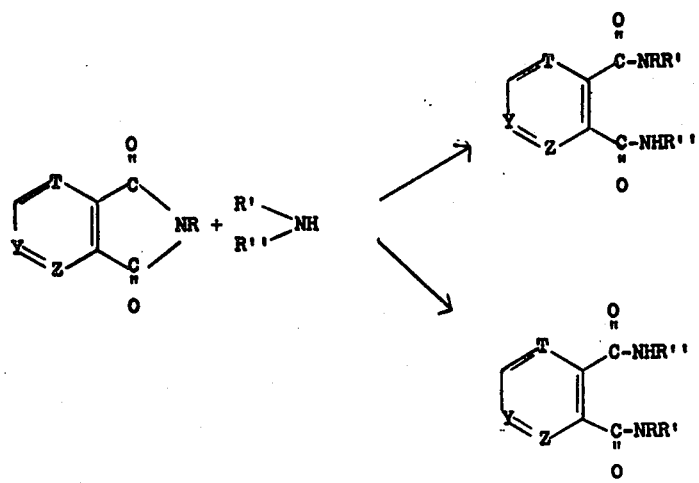

As is evident from the diagram set forth above, a mixture of compounds is conventionally produced because the imide ring in the starting compound can be and is normally broken at two points. The percent distribution of the various compounds formed will vary, depending on the nature of R' and R", the imide, and the solvent used.

For example, when an amine such as isopropyl amine is reacted with 2,3-pyridinedicarboximide (quinolinimide as it is otherwise known) two reaction products are formed. These are (1) $N^2$-isopropyl-2,3-pyridinedicarboxamide which can be separated by selective precipitation and (2) a mixture of (a) $N^2$-isopropyl-2,3-pyridinedicarboxamide and (b) $N^3$-isopropyl-2,3-pyridinedicarboxamide. This reaction can be illustrated as follows:

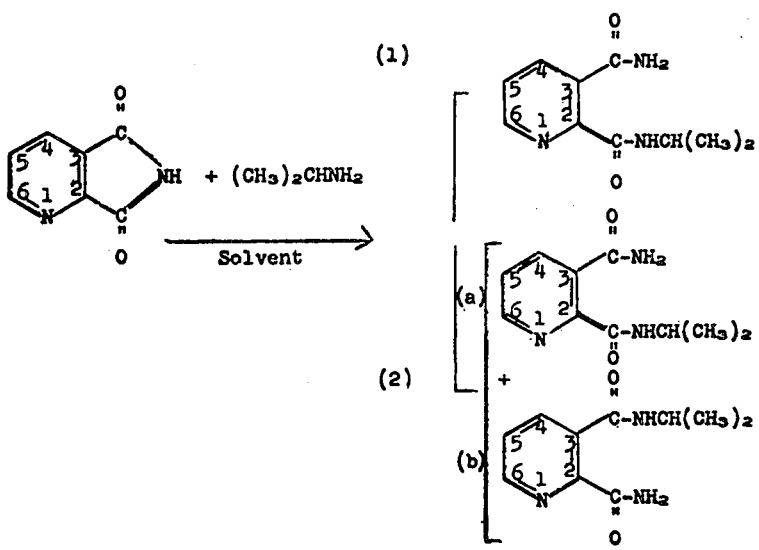

The ratio of $N^2$-isopropyl-2,3-pyridinedicarboxamide to $N^3$-isopropyl-2,3-pyridinedicarboxamide formed in the above reaction (including the $N^2$-isopropyl-2,3-pyridinecarboxamide separated by selective precipitation as well as that remaining in the mixture of $N^2$-isopropyl-2,3-pyridinedicarboxamide plus $N^3$-isopropyl-2,3-pyridinedicarboxamide) depends on the particular solvent used, as is explained in Example I herein.

The above illustrated reaction can be carried out at temperatures ranging from about 0° to 50°C.* in the presence of an anhydrous solvent. The solvent must be anhydrous in order to preclude the possibility of hydrolyzing the imide starting compound. Almost any anhydrous solvent can be used which will not react with amines or the imide starting compound or products produced. Benzene, however, has been found unsatisfactory for the purposes of the invention.

* All temperatures herein are in Centigrade degrees, and "parts" are parts by weight, unless otherwise indicated.

In the above reaction whee $N^2$-isopropyl-2,3-pyridinedicarboxamide and a mixture of $N^2$-isopropyl-2,3-pyridinedicarboxamide and $N^3$-isopropyl-2,3-pyridinedicarboxamide is being produced, the pure $N^2$-isopropyl-2,3-pyridinedicarboxamide being formed will ordinarily precipitate out of solution first, leaving the mixture in solution. The first product formed can then be separated by filtration. The mixture can then be separated from the solvent by vacuum distillation and the two constituents from each other by column chromatography.

The reaction of this invention is carried out for a sufficient period of time the form the desired products. This time will vary according to the particular product being formed. The reaction is exothermic in nature; however, external heating will shorten the reaction time.

For example, if isopropylamine is being reacted with 2,3-pyridinedicarboximide and ethanol is used as the solvent, it has been found that the reaction will go to completion in about 2 hours.

The preferred amines for use in the process of this invention are those which have branched chain carbons in the substituent group. The most preferred amine is sec-butylamine. Other preferred amines include cyclohexylamine, ethylamine, isopropylamine, benzylamine and cyclooctylamine.

When ammonia is used as a reactant instead of a primary or secondary amine, the preferred imide starting compound is N-isopropyl-2,3-pyridined:carboximide.

The preferred solvent is 2-propanol. Other preferred solvents are dimethylformamide, tetrahydrofuran and ethanol. Other suitable solvents include anhydrous ethers and high molecular weight alcohols.

This invention will be more fully understood by reference to the following examples, which describe preferred embodiments of the method of the invention. This invention is not limited thereby, however.

EXAMPLE I

PREPARATION OF $N^2$-ISOPROPYL-2,3-PYRIDINEDICARBOXAMIDE

A 250 ml., 3-necked flask equipped with a stirrer, thermometer and condenser fitted with a $CaCl_2$ drying tube, was charged, at room temperature, with 7.4 g. of 2,3-pyridinedicarboximide and 100 ml. of anhydrous ethanol. To the stirred reaction mixture was added, in one portion, 3.5 g. of isopropylamine. Within one hour, a clear brown solution was observed. After two hours, the solution was cooled to 2°C. whereupon solids formed. The solids were removed by filtration. The filtrate was concentrated to a volume of 10–15 ml. in vacuo and a second crop os solids removed by filtration. Both crops of solids were air dried under infrared lamps. The overall yield of material with m.p. 149°–153°C. was 46.2 percent. Recrystallization from acetone gave material with m.p. 151.5°–153°C. and an elemental analysis as follows:

|   | Theory | Found |
|---|--------|-------|
| C | 57.96% | 57.79% |
| H | 6.32%  | 6.28%  |
| N | 20.28% | 19.57% |

Further examination of this material by infrared techniques, as well as by chemical reactions, showed the material to be essentially $N^2$-isopropyl-2,3-pyridinedicarboxamide with at most, merely a trace of $N^3$-isopropyl-2,3-pyridinedicarboxamide.

Additional runs in anhydrous ethanol as solvent, in general, afforded 50–60 percent yields of essentially pure $N^2$-isopropyl-2,3-pyridinedicarboxamide, m.p. 151°–153° and in addition, 50–40 percent yields of a mixture of $N^2$-isopropyl-2,3-pyridinedicarboxamide and $N^3$-isopropyl-2,3-pyridinedicarboxamide, in which the former predominates.

Similar results were observed using anhydrous methanol as the reaction solvent.

When the above reaction was carried out in anhydrous 2-propanol, no first crop of essentially pure $N^2$-isopropyl-2,3-pyridinedicarboxamide could be isolated. In this case, nearly quantitative yields of a mixture of $N^2$- and $N^3$-amides was produced in which $N^2$-isopropyl-2,3-pyridinedicarboxamide predominated to the extent of 90–95 percent.

If the above reaction was performed in anhydrous tetrahydrofuran, a quantitative yield of a mixture of isomeric amides was produced but in this instance the isomer distribution was found to be 60–65 percent $N^2$-isopropyl-2,3-pyridinedicarboxamide, and 40–35 percent $N^3$-isopropyl-2,3-pyridinedicarboxamide.

When anhydrous benzene was employed as the reaction solvent in the above reaction, very little reaction occurred, the 2,3-pyridinedicarboximide being recovered essentially unchanged. The small amount of reaction whch did occur, afforded a mixture of isomeric amides, in essentially equal amounts.

EXAMPLE 2

PREPARATION OF $N^3$-ISOPROPYL-3,4-PYRIDINEDICARBOXAMIDE

A 250 ml. 3-necked flask equipped with a stirrer, condenser, thermometer, rotometer, drying tube and ice bath was charged with 5.0 g. N-isopropyl-3,4-pyridinedicarboximide and 80 ml. absolute ethanol. Ammonia gas from a cylinder was bubbled into the reaction mixture at the rate of 0.1–0.5 g./min. The temperature at this point was 4°. The ammonia was added for a period of 2 hours and 37 minutes, during which time the temperature was reduced to 0°. Excess gas was allowed to bubble off and the reaction mixture was then set aside in a freezer overnight. The next morning the reaction mixture was taken out of the freezer and concentrated in vacuo until a solid appeared. The white slid residue was removed by filtration and air dried. The yield was 3.2 g. of product having a melting point of 162°–164°. The recovery was 60 percent of theory.

The product (believed to be $N^3$-isopropyl-3,4-pyridinedicarboxamide) was recrystallized from benzene and the resulting product, m.p. 165°–167°, was subjected to elemental analysis, with the following results.

|   | Theory | Found |
|---|--------|-------|
| C | 57.96% | 57.87% |
| H | 6.32%  | 6.30%  |
| N | 20.28% | 19.71% |

Infrared analysis and chemical reactions suggested the assigned structure.

EXAMPLE 3

PREPARATION OF $N^3$-ISOPROPYL-2,3-PYRIDINEDICARBOXAMIDE

A 250 ml., 3-necked flask equipped with a stirrer, condenser, thermometer, drying tube, and gas inlet and outlet tubes, was charged with 5 g. N-isopropyl-2,3-pyridinedicarboximide and 80 ml. of absolute ethanol. The flask was then immersed in a cooling bath. Ammonia was then bubbled into the reaction mixture at the rate of 0.1–0.5 g./min. At this point the temperature of the reaction mixture was 5°. After 65 minutes of ammonia addition, the reaction mixture turned hazy and solids began to precipitate. At this point the temperature was 2.5°.

The ammonia addition was continued for a total of 2 hours and 35 minutes, and was then discontinued. The reaction was continued for an additional 5 hours, at which time the reaction mixture was filtered, and the filter cake then dried (the filtrate was set aside in a freezer). The yield was 0.8 g. of product having a melting point of 168°169°. Infrared analysis and chemical reactions showed this product to be in agreement with the structure of the desired $N^3$-isopropyl-2,3-pyridinedicarboxamide. The product had the following elemental analysis:

|   | Theory | Found |
|---|--------|-------|
| C | 57.96% | 57.65% |
| H | 6.32%  | 6.56%  |
| N | 20.27% | 19.82% |

The material which precipitated from the above filtrate was removed by filtration and air dried. The yield was 1.0 g. of product having a melting point of 168°–169°.

Infrared analysis indicated that this product was also $N^3$-isopropyl-2,3-pyridinedicarboxamide.

EXAMPLES 4 THROUGH 49

Numerous other compounds have been produced by the method of the invention. Information concerning starting materials, batch sizes, reaction conditions, final products and yields for representative ones of such preparations is presented in Table I, below.

TABLE I

| Ex. | Starting Imide | Grams | Amine | Grams | Solvent | Vol. in ml. | Reaction Temp. °C. | Reaction Time Hr. |
|-----|----------------|-------|-------|-------|---------|-------------|--------------------|-------------------|
| 4   | 2,3-pyridinedicarboximide | 14.8 | cyclohexylamine | 8.85 | tetrahydrofuran | 100 | 0–26 | 1.25 |
| 5   | 3,4-pyridinedicarboximide | 29.6 | isopropylamine  | 17.7 | ethanol         | 150 | 0–16 | 2.75 |

3,960,877

TABLE I-continued

| Ex. | Starting Imide | Grams | Amine | Grams | Solvent | Vol. in ml. | Reaction Temp. °C. | Reaction Time Hr. |
|---|---|---|---|---|---|---|---|---|
| 6 | N-isopropyl-3,4-pyridine-dicarboximide | 5.0 | ammonia | excess | ethanol | 80 | 1–0 | 2.5 |
| 7 | N-ethyl-2,3-pyridine-dicarboximide | 5.0 | ammonia | excess | ethanol | 80 | 2–6 | 4.5 |
| 8 | 2,3-pyridinedicarboximide | 29.6 | isopropylamine | 17.7 | tetrahydrofuran | 150 | 5–26 | 1.5 |
| 9 | 2,3-pyridinedicarboximide | 7.4 | ethylamine | 4.5 | ethanol | 100 | 22–27 | 1.5 |
| 10 | 2,3-pyridinedicarboximide | 20.7 | 3,4-dichloro-benzylamine | 25 | 2-propanol | 275 | 20–53 | 6 |
| 11 | 2,3-pyridinedicarboximide | 20.7 | 3,4-dichloro-benzylamine | 25 | 2-propanol | 275 | 20–53 | 6 |
| 12 | 2,3-pyridinedicarboximide | 20.7 | 2,4-dichloro-benzylamine | 25 | 2-propanol | 300 | 22–50 | 6 |
| 13 | 2,3-pyridinedicarboximide | 20.7 | 2,4-dichloro-benzylamine | 25 | 2-propanol | 300 | 22–50 | 6 |
| 14 | 2,3-pyridinedicarboximide | 26 | 4-chlorobenzyl-amine | 25 | 2-propanol | 275 | 20–53 | 6.5 |
| 15 | 2,3-pyridinedicarboximide | 26 | 4-chlorobenzyl-amine | 25 | 2-propanol | 275 | 20–53 | 6.5 |
| 16 | 2,3-pyridinedicarboximide | 25.2 | 3-chlorobenzyl-amine | 25 | 2-propanol | 275 | 23–52 | 7 |
| 17 | 2,3-pyridinedicarboximide | 25.2 | 3-chlorobenzyl-amine | 25 | 2-propanol | 275 | 23–52 | 7 |
| 18 | 2,3-pyridinedicarboximide | 26 | 2-chlorobenzyl-amine | 25 | 2-propanol | 250 | 22–53 | 9 |
| 19 | 2,3-pyridinedicarboximide | 25.9 | 4-methoxy-benzylamine | 25 | 2-propanol | 400 | 24–34 | 5.5 |
| 20 | 2,3-pyridinedicarboximide | 25.9 | 4-methoxybenzyl-amine | 25 | 2-propanol | 400 | 24–34 | 5.5 |
| 21 | 2,3-pyridinedicarboximide | 37 | 4-aminomethyl-pyridine | 27 | 2-propanol | 200 | 22–31 | 9 |
| 22 | 2,3-pyridinedicarboximide | 37 | 3-aminomethyl-pyridine | 29.2 | 2-propanol | 275 | 22–53 | 5.5 |
| 23 | 2,3-pyridinedicarboximide | 37 | 3-aminomethyl-pyridine | 29.2 | 2-propanol | 275 | 22–53 | 5.5 |
| 24 | 2,3-pyridinedicarboximide | 37 | d,l-α-methyl-benzylamine | 30.4 | 2-propanol | 200 | 22–27 | 30 |
| 25 | 2,3-pyridinedicarboximide | 37 | d,l-α-methyl-benzylamine | 30.4 | 2-propanol | 200 | 22–27 | 30 |
| 26 | 2,3-pyridinedicarboximide | 74.1 | methylamine | 15.6 | 2-propanol | 200 | 22–48 | 6 |
| 27 | 2,3-pyridinedicarboximide | 37 | methylamine | 7.8 | 2-propanol | 100 | 22–48 | 6.5 |
| 28 | 2,3-pyridinedicarboximide | 37 | 2-ethylhexylamine | 32.3 | 2-propanol | 100 | 23–41 | 5.5 |
| 29 | 2,3-pyridinedicarboximide | 37 | 2-ethylhexylamine | 32.3 | 2-propanol | 100 | 23–41 | 5.5 |
| 30 | 2,3-pyridinedicarboximide | 40 | propargylamine | 15 | 2-propanol | 100 | 24–34 | 8.5 |
| 31 | 2,3-pyridinedicarboximide | 40 | propargylamine | 15 | 2-propanol | 100 | 24–34 | 8.5 |
| 32 | 2,3-pyridinedicarboximide | 37 | cyclopropylamine | 14.3 | 2-propanol | 100 | 24–42 | 6 |
| 33 | 2,3-pyridinedicarboximide | 74.1 | benzylamine | 53.6 | 2-propanol | 300 | 22–52 | 5.5 |
| 34 | 2,3-pyridinedicarboximide | 37 | allylamine | 14.3 | 2-propanol | 100 | 26–52 | 5 |
| 35 | 2,3-pyridinedicarboximide | 37 | propylamine | 14.8 | 2-propanol | 100 | 23–46 | 5.5 |
| 36 | 2,3-pyridinedicarboximide | 37 | propylamine | 14.8 | 2-propanol | 100 | 23–46 | 5.5 |
| 37 | 2,3-pyridinedicarboximide | 14.8 | cyclooctylamine | 14 | 2-propanol | 75 | 23–28 | 24 |
| 38 | 2,3-pyridinedicarboximide | 14.8 | cyclooctylamine | 14 | 2-propanol | 75 | 23–28 | 24 |
| 39 | 2,3-pyridinedicarboximide | 29.6 | butylamine | 18.5 | 2-propanol | 125 | 3–16 | 2 |
| 40 | 2,3-pyridinedicarboximide | 29.6 | butylamine | 18.5 | 2-propanol | 125 | 3–16 | 2 |
| 41 | 2,3-pyridinedicarboximide | 14.8 | sec-butylamine | 8.6 | ethanol | 75 | 5–20 | 3.5 |
| 42 | 2,3-pyridinedicarboximide | 14.8 | sec-butylamine | 76 | 2-propanol | 400 | 25–41 | 6 |
| 43 | 2,3-pyridinedicarboximide | 14.8 | sec-butylamine | 11 | dimethylformamide | 50 | 23–43.5 | 3.5 |
| 44 | 2,3-pyrazinedicarboximide | 14.9 | cyclooctylamine | 14 | tetrahydrofuran | 150 | 22–35 | 3 |
| 45 | 2,3-pyrazinedicarboximide | 26.1 | isopropylamine | 11.8 | tetrahydrofuran | 200 | 21–37 | 4 |
| 46 | 2,3-pyrazinedicarboximide | 23.8 | butylamine | 14.6 | tetrahydrofuran | 175 | 24–45 | 4 |
| 47 | 2,3-pyrazinedicarboximide | 23.5 | cyclohexylamine | 19.8 | tetrahydrofuran | 450 | 26–47 | 2 |
| 48 | 2,3-pyrazinedicarboximide | 15 | sec-butylamine | 8.8 | tetrahydrofuran | 175 | 24–36 | 4 |
| 49 | 2,3-pyrazinedicarboximide | 19 | aniline | 14 | dimethylformamide | 30 | 23–147 | 4 |

| Ex. | Product | Grams | % Yield | Melting Point in degrees C. | Color | Theory C | Theory H | Theory N | Found C | Found H | Found N |
|---|---|---|---|---|---|---|---|---|---|---|---|
| 4 | N²-cyclohexyl-2,3-pyridinedicarboxamide | 16.7 | 68 | 123–125 | white | 63.14 | 6.93 | 16.99 | 63.33 | 7.09 | 16.78 |
| 5 | N⁴-isopropyl-3,4-pyridinedicarboxamide | 31.4 | 75.9 | 173–174 | white | 57.96 | 6.32 | 20.28 | 57.90 | 6.45 | 19.89 |
| 6 | Mixture of N⁴-isopropyl-3,4-pyridinedicarboxamide and N³-isopropyl-3,4-pyridinedicarboxamide | 4.8 | 88 | 160–167 | off white | — | — | — | — | — | — |
| 7 | N³-ethyl-2,3-pyridine-dicarboxamide | 2.0 | 36.4 | 175–176 | white | 55.95 | 5.73 | — | 56.09 | 5.73 | — |
| 8 | Mixture of N²-isopropyl-2,3-pyridinedicarboxamide and N³-isopropyl-2,3-pyridine dicarboxamide | 40.4 | 97.6 | 138.5–139.5 | cream | — | — | — | — | — | — |
| 9 | Mixture of N²-ethyl-2,3-pyridinedicarboxamide and N³-ethyl-2,3-pyridine-dicaboxamide | 6.2 | 64 | 122°–133° | cream | 55.95 | 5.73 | 21.75 | 55.49 | 5.92 | 21.53 |
| 10 | Mixture of N²-(3,4-dichloro-benzyl)-2,3-pyridinedicarboxamide and N³-(3,4-dichlorobenzyl)-2,3-pyridinedicarboxamide | 40.3 | 90 | 179–180(dec) | cream | — | — | — | — | — | — |
| 11 | N²-(3,4-dichlorobenzyl)-2,3-pyridinedicarboxamide | 34.3 | 85 | 187–188 | white | 51.87 | 3.42 | 12.96 | 51.98 | 3.43 | 12.92 |

3,960,877

TABLE I-continued

| Ex. | Product | Grams | % Yield | Melting Point in degrees C. | Color | Theory C | Theory H | Theory N | Found C | Found H | Found N |
|---|---|---|---|---|---|---|---|---|---|---|---|
| 12 | Mixture of $N^2$-(2,4-dichlorobenzyl)-2,3-pyridinedicarboxamide and $N^3$-(2,4-dichlorobenzyl)-2,3-pyridinedicarboxamide | 41.7 | 91.8 | 127–184(dec) | cream | — | — | — | — | — | — |
| 13 | $N^2$-(2,4-dichlorobenzyl)-2,3-pyridinedicarboxamide | 33.8 | 74 | 188–189 | white | 51.87 | 3.42 | 12.96 | 51.95 | 3.46 | 12.92 |
| 14 | Mixture of $N^2$-(4-chlorobenzyl)-2,3-pyridinedicarboxaide and $N^3$-(4-chlorobenzyl)-2,3-pyridinedicarboxamide | 44.2 | 87 | 171–172 | cream | — | — | — | — | — | — |
| 15 | $N^2$-(4-chlorobenzyl)-2,3-pyridinedicarboxamide | 39.8 | 78.5 | 178–179 | white | 58.04 | 4.17 | 14.50 | 57.84 | 4.07 | 14.34 |
| 16 | Mixture of $N^2$-(3-chlorobenzyl)-2,3-pyridinedicarboxamide and $N^3$-(3-chlorobenzyl)-2,3-pyridinedicarboxamide | 41.7 | 82 | 136–140 | cream | — | — | — | — | — | — |
| 17 | $N^2$-(3-chlorobenzyl)-2,3-pyridinedicarboxamide | 22.9 | 45 | 147–148 | white | 58.04 | 4.17 | 14.50 | 58.04 | 4.15 | 14.45 |
| 18 | $N^2$-(2chlorobenzyl)-2,3-pyridinedicarboxamide | 42.4 | 84 | 191–192 | white | 58.04 | 4.17 | 14.50 | 58.17 | 23.45 | 14.51 |
| 19 | Mixture of $N^2$-(4-methoxybenzyl)-2,3-pyridinedicarboxamide and $N^3$-(4-methoxybenzyl)-2,3-pyridinedicarboxamide | 50 | 90 | 141–144 | cream | — | — | — | — | — | — |
| 20 | $N^2$-(4-methoxybenzyl)-2,3-pyridinedicarboxamide | 32 | 64 | 155–156 | white | 63.15 | 5.30 | 14.73 | 63.02 | 5.35 | 14.83 |
| 21 | Mixture of $N^2$-(4-pyridylmethyl)-2,3-pyridinedicarboxamide and $N^3$-(4-pyridylmethyl)-2,3-pyridinedicarboxamide | 61.3 | 95.6 | 168.5–169.5 | white | 60.93 | 4.72 | 21.86 | 61.13 | 4.82 | 21.98 |
| 22 | Mixture of $N^2$-(3-pyridylmethyl-2,3-pyridinedicarboxamide and $N^3$-(3-pyridylmethyl)-2,3-pyridinedicarboxamide | 64.1 | 92 | 156.5–157.5 | cream | — | — | — | — | 13 | — |
| 23 | $N^2$-(3-pyridylmethyl)-2,3-pyridinedicarboxamide | 54.5 | 85 | 160–161 | white | 60.93 | 4.72 | 21.86 | 61.47 | 4.55 | 21.96 |
| 24 | $N^2$-($\alpha$-phenethyl)-2,3-pyridinedicarboxamide | 53.1 | 79 | 140–141 | white | 66.90 | 5.61 | 15.60 | 67.66 | 5.74 | 15.65 |
| 25 | Mixture of $N^2$-(2-phenethyl)-2,3-pyridinedicarboxamide and $N^3$-($\alpha$-phenethyl)-2,3-pyridinedicarboxamide | 57.8 | 85 | 84–145 | tan | — | — | — | — | — | — |
| 26 | $N^2$-methyl-2,3-pyridinedicarboxamide | 59 | 72 | 177.5–178 | white | 53.63 | 5.06 | 23.45 | 53.66 | 5.01 | 23.27 |
| 27 | Mixture of $N^2$-methyl-2,3-pyridinedicarboxamide and $N^2$-methyl-2,3-pyridinedicarboxamide | 45 | 89 | 172.5–175 | cream | — | — | — | — | — | — |
| 28 | $N^2$-(2-ethylhexyl)-2,3-pyridinedicarboxamide | 60.8 | 87.7 | 100–102 | white | 64.96 | 8.36 | 15.15 | 65.08 | 8.65 | 14.90 |
| 29 | Mixture of $N^2$-(2-ethylhexyl)-2,3-pyridinedicarboxamide and $N^3$-(2-ethylhexyl)-2,3-pyridinedicarboxamide | 64.3 | 93 | 99–105 | tan | — | — | — | — | — | — |
| 30 | $N^2$-(propargyl)-2,3-pyridinedicarboxamide | 26g | 47% | 186–187 | white | 58.82 | 4.92 | 20.58 | 58.51 | 4.02 | 20.44 |
| 31 | Mixture of $N^2$-(propargyl)-2,3-pyridinedicarboxamide and $N^3$-(propargyl)-2,3-pyridinedicarboxamide | 51.8 | 94 | 167–171 | cream | — | — | — | — | — | — |
| 32 | Mixture of $N^2$-(cyclopropyl)-2,3-pyridinedicarboxamide and $N^3$-(cyclopropyl)-2,3-pyridinedicarboxamide | 47.5 | 93 | 128–134 | cream | 58.53 | 5.40 | 20.48 | 58.37 | 5.16 | 20.08 |
| 33 | Mixture of $N^2$-benzyl-2,3-pyridinedicarboxamide and $N^3$-benzyl-2,3-pyridinedicarboxamide | 123 | 96.4 | 127–128 | cream | 65.87 | 5.13 | 16.46 | 66.13 | 5.34 | 16.32 |
| 34 | Mixture of $N^2$-allyl-2,3-pyridinedicarboxamide and $N^3$-allyl-2,3-pyridinedicarboxamide | 49.5 | 96.5 | 144–149 | white | 58.53 | 5.40 | 20.47 | 58.63 | 5.62 | 20.41 |
| 35 | Mixture of $N^2$-propyl-2,3-pyridinedicarboxamide and $N^3$-propyl-2,3-pyridinedicarboxamide | 42.3 | 81.7 | 105–112 | cream | — | — | — | — | — | — |
| 36 | $N^2$-propyl-2,3-pyridinedicarboxamide | 31.8 | 60 | 121–122 | white | 57.96 | 6.32 | 20.27 | 58.60 | 6.15 | 19.61 |
| 37 | $N^2$-cyclooctyl-2,3-pyridinedicarboxamide | 19.3 | 70 | 149–151 | white | 65.43 | 7.69 | 15.26 | 65.86 | 7.80 | 15.35 |
| 38 | Mixture of $N^2$-cyclooctyl-2,3-pyridinedicarboxamide and $N^3$-cyclooctyl-2,3-pyridinedicarboxamide | 26 | 93 | 114–151 | cream | — | — | — | — | — | — |
| 39 | $N^2$-butyl-2,3-pyridinedicarboxamide | 7 | 17 | 109–111 | white | 59.71 | 6.83 | 18.99 | 59.49 | 6.69 | 18.92 |
| 40 | Mixture of $N^2$-butyl-2,3-pyridinedicarboxamide and $N^3$-butyl-2,3-pyridinedicarboxamide | 35.1 | 79.4 | 87–110 | cream | — | — | — | — | — | — |

TABLE I-continued

| Ex. | Product | Grams | % Yield | Melting Point in degrees C. | Color | Theory C | H | N | Found C | H | N |
|---|---|---|---|---|---|---|---|---|---|---|---|
| | dicarboxamide | | | | | | | | | | |
| 41 | N²-(sec-butyl)-2,3-pyridinedicarboxamide | 7.8 | 35 | 114–115 | white | 59.71 | 6.83 | 18.99 | 59.66 | 6.88 | 18.80 |
| 42 | Mixture of N²-(sec-butyl)-2,3-pyridinedicarboxamide and N³-(sec-butyl)-2,3-pyridinedicarboxamide | 201 | 91 | 110–115 | cream | — | — | — | — | — | — |
| 43 | Mixture of N²-(sec-butyl)-2,3-pyridinedicarboxamide and N³-(sec-butyl)-2,3-pyridinedicarboxamide | 19.6 | 88.6 | 109–116 | cream | — | — | — | — | — | — |
| 44 | N-cyclooctyl-2,3-pyrazinedicarboxamide | 24.2 | 87.7 | 176–177 | white | 60.85 | 7.29 | 20.27 | 60.92 | 7.43 | 20.00 |
| 45 | N-isopropyl-2,3-pyrazinedicarboxamide | 35.6 | 97.8 | 180–182 | white | 51.92 | 5.81 | 26.91 | 51.82 | 5.80 | 27.06 |
| 46 | N-butyl-2,3-pyrazinedicarboxamide | 34.4 | 97.8 | 180–182 | white | 54.04 | 6.35 | 25.21 | 54.49 | 6.65 | 25.40 |
| 47 | N-cyclohexyl-2,3-pyrazinedicarboxamide | 37.5 | 98.7 | 184–186 | white | 58.05 | 6.49 | 22.56 | 58.50 | 6.76 | 22.32 |
| 48 | N-(sec-butyl)-2,3-pyrazinedicarboxamide | 17.8 | 80 | 144–146 | white | 54.04 | 6.35 | 25.21 | 53.93 | 6.37 | 25.02 |
| 49 | N-phenyl-2,3-pyrazinedicarboxamide | 8 | 25 | 178–180 | white | 59.50 | 4.16 | 23.13 | 59.67 | 4.41 | 23.09 |

The other compounds which fall within the scope of those which can be prepared by the method of the invention, can be prepared in essentially the same manner so described in Example 1 or 2 with appropriate substitutions being made for the isopropylamine used in Example 1 or N-isopropyl-3,4-pyridinedicarboximide used in Example 2.

The imide starting materials used in practicing the method of this invention can be prepared from corresponding 2,3- and 3,4-pyridinedicarboxylic acids and 2,3-pyrazinedicarboxylic acids according to the method outlined below.

A quantity of commercially available 2,3-pyridinedicarboxylic acid, is reacted with a mixture of an excess of acetic anhydride and an excess of acetamide to produce the imide. It is desirable to use about twice as much acetic anhydride and about three times as much acetamide as is stoichiometrically required to react with the dicarboxylic acid starting compound.

In carrying out the process all of the reactants are charged, more or less simultaneously, into the reaction vessel and stirring is begun and continued throughout the reaction. Heat is then applied to bring the temperature of the reaction mixture to one in the range of 130°–140° and it is held at a temperature in that range for ½ hour. During this period, acetic acid (b.p. 118°), which is one of the reaction by-products, is continually boiled off at the temperature at which the reaction is conducted.

This reaction can be illustrated as follows:

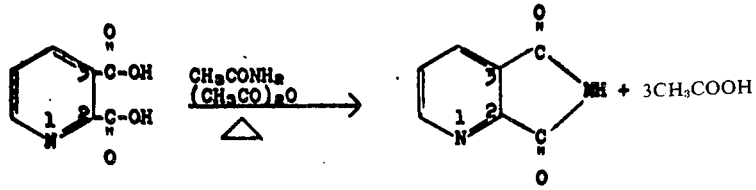

2,3-pyridinedicarboxylic acid → 2,3-pyridinedicarboximide

The 3,4-pyridinedicarboximides and 2,3-pyrazinedicarboximides also used as starting materials in the method of this invention can be prepared in a similar manner from other dicarboxylic acid starting materials.

The N-substituted-2,3-pyridinedicarboximides, -3,4-pyridinedicarboximides, and -2,3-pyrazinedicarboximides used as starting compounds can be prepared in the manner described in a copending application entitled "Method for Producing Heterocyclic Dicarboximides", Serial No. 740,080, filed June 26, 1968, now U.S. Pat. No. 3,525,747 dated Aug. 25, 1970. These compounds are produced by anhydrous alkylation of the imide precursor with an organic halide in the presence of sodium hydride and a suitable solvent.

As stated herein the compounds produced by the method of this invention are useful intermediates in the production of herbicidally active 3-substituted pyrido[3,2-d]pyrimidine-2,4(1H,3H)-diones, as well as some of the 82,3d-], [4,3-d] and [3,4-d] series, plus certain lumazines. The preparation of 3-isopropyl-pyrido[3,2-d]pyrimidine-2,4(1H,3H)-dione from N²-isopropyl-2,3-pyridinedicarboxamide, a compound produced by the method of the invention, will be described.

EXAMPLE A

PREPARATION OF 3-ISOPROPYL-PYRIDO[3,2-d]PYRIMIDINE-2,4(1H;3H)-DIONE

A 22 l. flask equipped with a stirrer and a thermometer, and surrounded by a heating mantle was charged with 8 l. water, 398 g. sodium hydroxide and 9.5 l. aqueous solution containing 595 g. NaOCl. Stirring was commenced, and was continued throughout the reaction. When this charging was complete, the temperature of the charge was 31°; then, 1.76 Kg. N²-isopropyl-2,3-pyridinedicarboxamide was added to the NaOCl-NaOH solution in the flask. After the pyridinedicarboxamide dissolved, the temperature of the reaction mixture was 33°; the reaction mixture was then heated for a total of about 55 minutes. The temperature after 10 minutes of heating was 40°, after 15 minutes 44°, after 21 minutes 52°, after 25 minutes, 60°, and, after 55 minutes 63°. The heating mantle was then removed, and the flask was immersed in an ice bath for about 2 hours 50 minutes; the final temperature of the reaction product was 10°. The reaction mixture was then acidified by making a gradual addition of glacial acetic acid to a pH of 6. The rate of addition of acetic acid and controlled so that the temperature of the reaction mixture in the flask remained within the range of 10 to 15°. The 3-isopropyl-pyrido[3,2-d]pyrimidine-2,4(1H,3H)-dione product, which had separated as an off-white to cream precipitate, was separated from the mother liquor by filtration, using a Buchner funnel. The final product was washed with tap water and dried in a circulating air oven in which the air was maintained at a temperature within the range of 80° to 100°.

The total recovery of dry product, melting point 238°–244°, amounted to 1.48 Kg., or 89.8 percent of theory. It was determined by nuclear magnetic resonance analysis that the product was 87 percent, plus or minus 10 percent, 3-isopropyl-pyrido[3,2-d]pyrimidine-2,4(1H,3H)-dione. The remainder of the product was 3-isopropyl-pyrido[2,3]pyrimidine-2,4(1H,3H)-dione. The presence of the [2,3-d]-family compound is attributable to an impurity in the amide starting material.

Other diones or lumazines can be produced in a similar manner from the other amide intermediates produced by the method of the invention.

All of the 3-substituted compounds of the pyrido[3,2-d]pyrimidine-2,4(1H,3H)-dione and lumazine families made from intermediate amides produced by the method of this invention have an unexpectedly high order of herbicidal activity. They have been found to be useful in controlling undesirable plants of both the monocotyledonous and the dicotyledonous species on either a postemergence or a preemergence basis.

By "preemergence" is meant that the compound is applied to the soil prior to emergence of the weed species sought to be controlled. This term, as used herein, also means the application of the herbicidal compounds falling within the scope of this disclosure to areas wherein useful or desirable plants are either growing or have been sown, but where the undesirable plants sought to be controlled have not as yet emerged.

By the term "postemergence" is meant that the compound is applied to the plant sought to be controlled after it has emerged from the soil surface. This term is also used to describe the application of herbicidally active compounds to soil surface in and around growing plants sought to be controlled for purposes of effecting root absorption by the undesirable plant species.

Especially active are the 3-substituted-pyrido[3,2-d]pyrimidine-2,4(1H,3H)-dione compounds where the 3-substituent is isopropyl, sec-butyl, cyclohexyl, or benzyl.

The preemergence and postemergence herbicidal activity of 3-isopropyl-pyrido[3,2-d]pyrimidine-2,4(1H,3H)-dione achieved at various application rates is shown in Table II below.

In using the compound, seeds of the types of plants set forth in Table II were sown in fresh soil. In the preemergence test the soil was sprayed with a solution of the test compound immediately after the seeds were planted, and before any noticeable growth developed. The solution was about a 2 percent by weight solution of the compound in acetone and/or alcohol. The compound was applied at the rate of 16 pounds per acre of soil surface.

Approximately 3 weeks after spray application, the herbicidal activity of the compound was determined by visual observation of the treated area in comparison with untreated control areas. These observations are reported below in Table II wherein the average activity rating is reported as the percent control of plant growth.

In the postemergence test the soil and developing plants were sprayed approximately 2 weeks after the seeds were sown. The compound was applied at the rate of 8 pounds per acre from about a 2 percent by weight solution of the test compound in acetone and/or alcohol. The postemergence herbicidal activity was measured in the same way as the preemergence activity; i.e. visual observation approximately 11 days after spraying, and expressed as the percent control of plant growth.

TABLE II

|  | Preemergence Treatment % Control | Postemergence Treatment % Control |
|---|---|---|
| Alfalfa | 100 | 90 |
| Corn | 100 | 30 |
| Wild Oats | 100 | 70 |
| Cheatgrass | 100 | 50 |
| Foxtail | 100 | 100 |
| Barnyard Grass | 100 | 80 |
| Crabgrass | 100 | 100 |
| Nutgrass 20 | 50 |  |
| Johnsongrass | 100 | 90 |
| Curled Dock | 100 | 100 |
| Snapbeans | 100 | 90 |
| Yellow Rocket | 100 | 100 |
| Chickweed | 100 | 70 |
| Cucumber | 100 | 100 |
| Pigweed | 100 | 100 |
| Velvetleaf | 100 | 100 |
| Lambsquarters | 90 | 100 |

The same solutions of the same compound can also be sprayed, for example along railroad right-of-ways, at an application rate of about 10 to 16 pounds per acre as a total herbicide, i.e., to prevent all vegetation. The other compounds prepared by a process utilizing the intermediates produced according to the method of the invention can be used as preemergence or postemergence herbicides in a similar manner. In the case of 3-cyclohexyl-pyrido[3,2-d]pyrimidine-2,4(1H,3H)-dione and 3-sec-butyl-pyrido[3,2-d]pyrimidine-2,4(1H,3H)-dione, substantially the same application rates, e.g., as similar or salt solutions in water, are effective; this is also generally true of the other members of the pyrido[3,2d-]pyrimidine-2,4(1H,3H)-dione family, although slightly higher application rates may be required. 3-benzyl-pyrido[3,2-d]pyrimidine-[2,4(1H,3H)-dione has been found to be peculiarly effective because of its selectivity; for example, applied as described above, at an application rate of 16 pounds per acre, the benzyl compound showed no preemergence herbicidal activity against cucumbers, corn or snapbeans, but total preemergence activity against alfalfa, cheatgrass, crabgrass, curled dock, chickweed, pigweed and lambsquarters.

Information concerning the compounds prepared by a process utilizing intermediates prepared according to the method of the invention, applied as described, and discussed above as having an unexpectedly high order of herbicidal activity, is presented in the following table.

TABLE III

| | pyrido[3,2-d] pyrimidine-2,4(1H,3H)-dione (Control) | | 3-ethyl-pyrido[3,2-d] pyrimidine-2,4(1H,3H)-dione | | 3-propyl-pyrido[3,2-d] pyrimidine-2,4(1H,3H)-dione | | 3-butyl-pyrido[3,2-d] pyrimidine-2,4(1H,3H)-dione | | 3-sec-butyl pyrido[3,2-d] pyrimidine-2,4(1H,3H)-dione | | 3-allyl-pyrido[3,2-d] pyrimidine-2,4(1H,3H)-dione | | 3-(2-ethylhexyl) pyrido[3,2-d] pyrimidine-2,4(1H,3H)-dione | |
|---|---|---|---|---|---|---|---|---|---|---|---|---|---|---|
| | Pre* (% Control) | Post** (% Control) | Pre (% Control) | Post (% Control) | Pre (% Control) | Post (% Control) | Pre (% Control) | Post (% Control) | Pre (% Control) | Post (% Control) | Pre (% Control) | Post (% Control) | Pre (% Control) | Post (% Control) |
| Alfalfa | 0 | 0 | 100 | 50 | 100 | 100 | 100 | 50 | 100 | 100 | 100 | 100 | 0 | 0 |
| Corn | 0 | 0 | 10 | 10 | 100 | 60 | 100 | 50 | 100 | 90 | 50 | 30 | 0 | 0 |
| Wild Oats | 0 | 0 | 100 | 0 | 100 | 90 | 100 | 100 | 100 | 100 | 100 | 20 | 0 | 0 |
| Cheatgrass | 0 | 0 | 100 | 30 | 100 | 100 | 100 | 100 | 100 | 100 | 100 | 30 | 0 | 0 |
| Foxtail | 0 | 0 | 40 | 40 | 100 | 100 | 100 | 100 | 100 | 100 | 90 | 100 | 0 | 0 |
| Barnyardgrass | 0 | 0 | 40 | 10 | 100 | 100 | 100 | 100 | 100 | 100 | 90 | 100 | 0 | 0 |
| Crabgrass | 0 | 0 | 100 | 80 | 100 | 100 | 90 | 100 | 100 | 100 | 100 | 100 | 10 | 10 |
| Nutgrass | 0 | 0 | 10 | 10 | 20 | 70 | 100 | 90 | 100 | 100 | 20 | 30 | 0 | 0 |
| Johnsongrass | 0 | 0 | 60 | 60 | 100 | 100 | 100 | 100 | 100 | 100 | 90 | 100 | 0 | 0 |
| Curled Dock | 0 | 0 | 100 | 90 | 100 | 100 | 90 | 100 | 100 | 100 | 100 | 100 | 0 | 10 |
| Snapbeans | 0 | 0 | 100 | 80 | 100 | 100 | 100 | 100 | 100 | 100 | 100 | 100 | 0 | 0 |
| Yellow Rocket | 0 | 0 | 100 | 100 | 100 | 100 | 100 | 90 | 100 | 100 | 100 | 100 | 90 | 90 |
| Chickweed | 0 | 0 | 100 | 100 | 100 | 100 | 100 | 100 | 100 | 100 | 100 | 100 | 70 | 50 |
| Cucumber | 0 | 0 | 100 | 50 | 100 | 100 | 100 | 100 | 100 | 100 | 100 | 100 | 10 | 20 |
| Pigweed | 0 | 0 | 100 | 90 | 100 | 100 | 100 | 90 | 100 | 100 | 100 | 100 | 0 | 100 |
| Velvetleaf | 0 | 0 | 90 | 100 | 100 | 100 | 100 | 100 | 100 | 100 | 90 | 100 | 0 | 0 |
| Lambsquarters | 0 | 0 | 100 | 100 | 100 | 100 | 70 | 10 | 100 | 100 | 100 | 100 | 30 | 100 |

| | 3-cyclopropyl pyrido[3,2-d] pyrimidine-2,4(1H,3H)-dione | | 3-cyclohexyl-pyrido[3,2-d] pyrimidine-2,4(1H,3H)-dione | | 3-cyclooctyl-pyrido[3,2-d] pyrimidine-2,4(1H,3H)-dione | | 3-benzyl pyrido[3,2-d] pyrimidine-2,4(1H,3H)-dione | |
|---|---|---|---|---|---|---|---|---|
| | Pre (% Control) | Post (% Control) | Pre (% Control) | Post (% Control) | Pre (% Control) | Post (% Control) | Pre (% Control) | Post (% Control) |
| Alfalfa | 100 | 0 | 100 | 30 | 100 | 60 | 100 | 0 |
| Corn | 10 | 0 | 90 | 40 | 50 | 0 | 10 | 0 |
| Wild Oats | 80 | 160 | 100 | 100 | 100 | 40 | 30 | 0 |
| Cheatgrass | 100 | 0 | 100 | 80 | 100 | 30 | 100 | 0 |
| Foxtail | 10 | 0 | 100 | 100 | 100 | 80 | 90 | 0 |
| Barnyardgrass | 10 | 0 | 100 | 100 | 190 | 90 | 90 | 0 |
| Crabgrass | 100 | 10 | 100 | 100 | 100 | 100 | 100 | 40 |
| Nutgrass | 0 | 0 | 100 | 100 | 20 | 40 | 0 | 0 |
| Johnsongrass | 10 | 0 | 100 | 100 | 100 | 100 | 90 | 0 |
| Curled Dock | 100 | 10 | 100 | 100 | 100 | 100 | 100 | 0 |
| Snapbean | 100 | 0 | 100 | 80 | 100 | 90 | 10 | 0 |
| Yellow Rocket | 100 | 100 | 100 | 100 | 100 | 100 | 90 | 70 |
| Chickweed | 100 | 100 | 100 | 100 | 100 | 100 | 100 | 100 |
| Cucumber | 100 | 20 | 100 | 100 | 90 | 100 | 0 | 10 |
| Pigweed | 100 | 90 | 100 | 100 | 100 | 100 | 100 | 100 |
| Velvetleaf | 100 | 0 | 100 | 100 | 100 | 100 | 90 | 30 |
| Lambsquarters | 100 | 100 | 100 | 100 | 100 | 100 | 100 | 60 |

| | Lumazine, 3-isopropyl | | Lumazine, 3-butyl | | Lumazine, 3-sec-butyl | | Lumazine, 3-cyclohexyl | | Lumazine, 3-cyclooctyl | |
|---|---|---|---|---|---|---|---|---|---|---|
| | Pre (% Control) | Post (% Control) | Pre (% Control) | Post (% Control) | Pre (% Control) | Post (% Control) | Pre (% Control) | Post (% Control) | Pre (% Control) | Post (% Control) |
| Alfalfa | 100 | 0 | 0 | 0 | 100 | 50 | 100 | 100 | 100 | 10 |
| Corn | 10 | 0 | 0 | 0 | 10 | 0 | 40 | 10 | 30 | 10 |
| Wild Oats | 10 | 0 | 0 | 0 | 30 | 0 | 20 | 10 | 100 | 10 |
| Cheatgrass | 10 | 0 | 0 | 0 | 90 | 0 | 10 | 50 | 100 | 0 |
| Foxtail | 10 | 0 | 0 | 0 | 30 | 0 | 20 | 10 | 40 | 50 |
| Barnyardgrass | 0 | 0 | 0 | 0 | 40 | 0 | 20 | 10 | 70 | 90 |
| Crabgrass | 70 | 0 | 0 | 0 | 100 | 0 | 80 | 20 | 90 | 100 |
| Nutgrass | 0 | 0 | 0 | 0 | 40 | 0 | 100 | 100 | 30 | 10 |
| Johnsongrass | 70 | 0 | 0 | 0 | 40 | 0 | 30 | 20 | 90 | 100 |
| Curled Dock | 100 | 0 | 0 | 0 | 70 | 50 | 90 | 100 | 100 | 100 |
| Snapbeans | 90 | 30 | 20 | 0 | 90 | 20 | 100 | 100 | 100 | 100 |
| Yellow Rocket | 100 | — | 0 | 70 | 100 | 100 | 100 | 100 | 100 | 100 |
| Chickweed | 60 | 0 | 90 | 0 | 40 | 0 | 100 | 90 | 100 | 100 |
| Cucumber | 100 | 10 | 0 | 0 | 10 | 60 | 100 | 100 | 100 | 100 |
| Pigweed | 100 | 0 | 0 | 0 | 100 | 20 | 100 | 90 | 100 | — |
| Velvetleaf | 100 | 0 | 0 | 0 | 100 | 90 | 100 | 100 | 100 | 100 |
| Lambsquarters | 100 | 40 | 0 | 70 | 100 | 100 | 100 | 100 | 100 | 100 |

*Preemergence test: compound applied at rate of 16 lb/acre
**Postemergence test: compound applied at rate of 8 lb/acre Of the members of the pyrido[2,3-d]pyrimidinedione family investigated, only 3-ethyl-pyrido[2,3-d]pyrimidine-2,4(1H,3H)-dione has been found to have herbicidal activity, and that only of a comparatively low order. For example, applied as described, at an application rate of 16 pounds per acre, the indicated compound was found to provide 100 percent control against snapbeans, 80 percent against chickweed, 80 percent against velvet leaf, 90 percent against nutgrass, and 80 percent against yellow rocket. In addition it had 100 percent control against volunteer soybeans. However, it had no significant control against cheatgrass, wild oats, foxtail, barnyardgrass, corn, alfalfa, johnsongrass, curled dock, pigweed, cucumber crabgrass or lambsquarters.

The following members of the [2,3-d], of the [4,3-d] and of the [3,4-d] families have been investigated at application rates of 16 pounds per acre, applied as described above, and have been found to have no appreciable herbicidal activity:

3-isopropyl-pyrido[2,3-d]pyrimidine-2,4(1H,3H)-
dione
3-phenyl-pyrido[2,3-d]pyrimidine-2,4(1H,3H)-
dione
3-cyclohexyl-pyrido[2,3-d]pyrimidine-2,4-(1H,3H)-
dione
3-isopropyl-pyrido[4,3-d]pyrimidine-2,4(1H,3H)-
dione
3-isopropyl-pyrido[3,4-d]pyrimidine-2,4(1H,3H)-
dione It will be appreciated from the foregoing discussion that the pyrido[3,2-d]pyrimidine-2,4-(1H,3H)-dione and the lumazine families of compounds for which the amides produced by the method of the invention are intermediates have unexpected utility as herbicides, and that this unexpected utility prevails throughout the families of compounds made from the amide intermediates produced by the claimed method. For example, the showing of a high order of herbicidal activity for $C_2$ through $C_8$ alkyl substituents in the 3-position (3-substituted-pyrido[3,2-d]pyrimidine-2,4(1H,3H)-dione family) and the demonstration that allyl, as a 3-substituent, has substantially the same order of activity as does an isopropyl substituent in the 3 position shows that alkenyl substituents in the same position impart activity of the same order as is imparted by alkyl substituents and, therefore, demonstrates utility for 3 alkenyl substituents having not more than 8 carbon atoms. Similarly, the demonstration of a high order of activity where the 3-substituent, in the indicated family, is a cycloalkyl group having 3 carbons, 6 carbons and 8 carbons demonstrates the high order of activity for such compounds where the 3-substituent is a cycloalkyl group having from 3 to 12 carbon atoms. Further, the demonstration of selectivity for a 3 benzyl substituent, as well as the showing of a high order of activity therefor, demonstrates utility for aralkyl substituents in the indicated position.

The compounds made from amido intermediates produced by the method of the invention which are not unexpectedly useful as herbicides are unexpectedly useful because of their close similarity, from a structural chemical standpoint, to compounds having extremely high orders of activity. This close structural similarity can be appreciated from a consideration of the following formulas:

1)

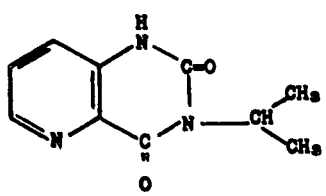

3-isopropyl-pyrido[3,2d-]pyrimidine-2,4(1H,3H)-
dione (has a high order of activity)

2)

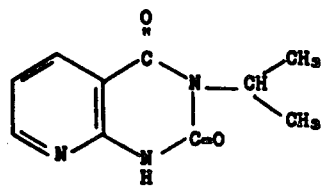

3-isopropyl-pyrido[2,3-d]pyrimidine-2,4(1H,3H)-
dione (has no appreciable activity)

The close structural similarities, coupled with the fact reported herein of the significant difference in order of herbicidal activity provides the basis for an orderly investigation, on the basis of molecular models, of the relation ship between chemical structure and herbicidal activity, the development of a theory explaining this relationship, and consequent significant advance in the useful arts on the basis of intelligent application of the theoretical explanation by skilled workers in the art.

It will be apparent that various changes and modifications can be made from the specific details set forth herein without departing from the spirit and scope of the invention as defined in the appended claims.

What I claim is:

1. A compound of the formula a)  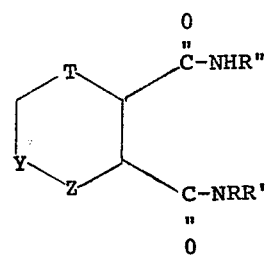   and   b) 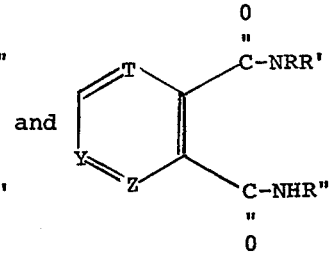

wherein each of T, Y and Z is nitrogen or CH and at least one is CH and at least one is nitrogen, and wherein when Y is nitrogen, T and Z are CH; and wherein one of R and R' is hydrogen and the other is a branched chain alkyl group having from 3 to 8 carbon atoms.

2. The (b) compound of claim 1 wherein R and R' are hydrogen.

3. The compound of claim 2 wherein T and Y are CH, Z is nitrogen, and the alkyl group is isopropyl or sec-butyl.

* * * * *